(12) United States Patent
Fuller et al.

(10) Patent No.: US 11,491,325 B2
(45) Date of Patent: Nov. 8, 2022

(54) STIMULATING SPINAL CORD MOTOR NEURONS USING ELECTRICAL SIGNALS

(71) Applicant: UNIVERSITY OF FLORIDA RESEARCH FOUNDATION, INCORPORATED, Gainesville, FL (US)

(72) Inventors: David D. Fuller, Gainesville, FL (US); Kevin Otto, Gainesville, FL (US); Michael D. Sunshine, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 0 days.

(21) Appl. No.: 16/640,859

(22) PCT Filed: Sep. 5, 2018

(86) PCT No.: PCT/US2018/049474
§ 371 (c)(1),
(2) Date: Feb. 21, 2020

(87) PCT Pub. No.: WO2019/050896
PCT Pub. Date: Mar. 14, 2019

(65) Prior Publication Data
US 2020/0368523 A1  Nov. 26, 2020

Related U.S. Application Data

(60) Provisional application No. 62/635,867, filed on Feb. 27, 2018, provisional application No. 62/554,277, filed on Sep. 5, 2017.

(51) Int. Cl.
*A61N 1/36* (2006.01)
*A61N 1/05* (2006.01)
*A61N 1/32* (2006.01)

(52) U.S. Cl.
CPC .......... *A61N 1/0551* (2013.01); *A61N 1/323* (2013.01); *A61N 1/3611* (2013.01); *A61N 1/36171* (2013.01); *A61N 1/36003* (2013.01)

(58) Field of Classification Search
CPC .... A61N 1/0551; A61N 1/323; A61N 1/3611; A61N 1/36171; A61N 1/36003
See application file for complete search history.

(56) References Cited

U.S. PATENT DOCUMENTS 5,081,989 A    1/1992  Graupe et al.
8,738,142 B2 * 5/2014  Palermo ............... A61N 1/0492
                                                   607/46

(Continued)

FOREIGN PATENT DOCUMENTS

WO    WO-2016/147643 A1    9/2016

OTHER PUBLICATIONS

International Searching Authority, International Search Report and Written Opinion for International Application No. PCT/US2018/049474, dated Mar. 15, 2019, (20 pages), Republic of Korea.

(Continued)

*Primary Examiner* — Michael W Kahelin
*Assistant Examiner* — Michael A Rizzuto
(74) *Attorney, Agent, or Firm* — Alston & Bird LLP

(57) ABSTRACT

An example system for exciting a selected set of motor neurons of a patient comprises one or more signal generators configured for generating a first electrical signal and a second electrical signal; a first set of wires configured to provide the first electrical signal to a first set of electrodes, wherein the first set of electrodes are configured for being (Continued)

secured to a first set of positions on the patient; a second set of wires configured to provide the second electrical signal to a second set of electrodes, wherein the second set of electrodes are configured for being secured to a second set of positions on the patient; and a controller configured to control operation of the one or more signal generators. The first electrical signal is a periodic signal of a first frequency. The second electrical signal is a periodic signal of a second frequency. The first frequency and the second frequency differ by a non-zero frequency difference. The first signal is provided to the first electrodes and the second signal is provided to the second electrodes for exciting the set of motor neurons of the patient.

37 Claims, 8 Drawing Sheets

(56) References Cited

U.S. PATENT DOCUMENTS

| | | | |
|---|---|---|---|
| 9,393,409 B2 | 7/2016 | Edgerton et al. | |
| 9,427,585 B2 | 8/2016 | Gliner | |
| 2009/0254144 A1* | 10/2009 | Bhadra | A61N 1/36007 607/41 |
| 2010/0114260 A1* | 5/2010 | Donofrio | A61N 1/0551 607/2 |
| 2012/0310303 A1 | 12/2012 | Popovic et al. | |
| 2013/0035745 A1 | 2/2013 | Ahmed et al. | |
| 2014/0163660 A1* | 6/2014 | Fang | A61N 1/36071 607/117 |
| 2016/0030737 A1 | 2/2016 | Gerasimenko et al. | |
| 2016/0121109 A1 | 5/2016 | Edgerton et al. | |
| 2016/0243365 A1 | 8/2016 | Kramer et al. | |
| 2017/0197081 A1* | 7/2017 | Charlesworth | A61N 1/36034 |
| 2018/0071528 A1 | 3/2018 | Fujiwara et al. | |
| 2018/0185642 A1* | 7/2018 | Lu | A61N 1/05 |

OTHER PUBLICATIONS

Lindquist, Susan Barber. "Man Moves Paralyzed Legs Using Device That Stimulates Spinal Cord," *Science Daily*, Mayo Clinic, Apr. 3, 2017, (4 pages), (article, online), [Retrieved from the Internet May 4, 2022] <URL: https://www.sciencedaily.com/releases/2017/04/170403123621.htm>.

Kern, Margot. "Paralyzed Men Move Legs With New Non-Invasive Spinal Cord Stimulation," *National Institutes of Health*, Jul. 30, 2015, (6 pages), (article, online), [Retrieved from the Internet May 4, 2022] <URL: https://www.nih.gov/news-events/news-releases/paralyzed-men-move-legs-new-non-invasive-spinal-cord-stimulation.

* cited by examiner

STIMULATING SPINAL CORD MOTOR NEURONS USING ELECTRICAL SIGNALS

CROSS REFERENCE TO RELATED APPLICATIONS

This application is a National Stage Application, filed under 35 U.S.C. § 371, of International Application No. PCT/US2018/049474, filed Sep. 5, 2018, which claims priority to U.S. Provisional Application No. 62/635,867, filed Feb. 27, 2018, and U.S. Provisional Application No. 62/554,277, filed Sep. 5, 2017; the contents of both of which are hereby incorporated by reference in their entirety.

BACKGROUND

Following spinal cord injury, voluntary activation of spinal cord motor neurons is often impossible. This causes paralysis of the spinal cord injury patient. When this paralysis affects muscles such as the diaphragm, the patient may require medical intervention, such as a ventilator to stay alive. However, keeping a patient connected to a ventilator may diminish a patient's mobility and ability to participate in various activities. For example, if a patient requires a ventilator, it may be difficult for that patient's wheelchair to be rolled outside to enjoy an outdoor event and/or the like.

Thus, there are further needs in the art for methods, apparatuses, systems, and/or the like for providing treatment to paralyzed muscles.

SUMMARY

According to an example embodiment, multiple (e.g., two) periodic electrical signals are provided to electrodes secured to specific locations on the patient to stimulate selected motor neurons. For example, the electrical signals may be sine waves. In an example embodiment, the periodic electrical signals are high frequency electrical signals (e.g., greater than 1 kHz) and are offset from one another by an offset frequency in the range of, for example, 1 to 100 Hz. For example, applying the periodic electrical signals results in a temporal interference pattern that has a frequency within the range of 1 to 100 Hz. The temporal interference pattern may cause one or more selected sets of motor neurons to be excited. The placement of the electrodes on the patient to which the signals are provided effectively selects the one or more sets of motor neurons to be excited. In an example embodiment, subcutaneous and/or "non-invasive" (e.g., secured to a patient's skin using adhesive) electrodes are used for delivering temporal interference currents for activation of the diaphragm. The ease and rapidity of subcutaneous electrode placement make subcutaneous temporal interference stimulation a potential short-term solution to severe hypoventiliation after acute neurological injury, drug overdose, and/or a "first responder" situation, and/or a potentially useful adjunct to respiratory rehabilitation.

According to an aspect of the present invention, a system for exciting a select set of motor neurons of a patient is provided. In an example embodiment, the system comprises a first signal generator configured to generate a first electrical signal; a first set of wires configured to provide the first electrical signal to a first set of electrodes secured to a first set of positions on a patient; a second signal generator configured to generate a second electrical signal; a second set of wires configured to provide the second electrical signal to a second set of electrodes secured to a second set of positions on a patient; and a controller configured to control operation of the first signal generator and the second signal generator. The first electrical signal is a periodic signal of a first frequency. The second electrical signal is a periodic signal of a second frequency. The first frequency and the second frequency differ by a non-zero frequency difference. Providing the first signal to the first electrodes and the second signal to the second electrodes excites a set of motor neurons of the patient.

According to another aspect of the present invention, a method for exciting a select set of motor neurons of a patient is provided. In an example embodiment, the method comprises causing a first signal generator to generate a first electrical signal; causing a second signal generator to generate a second electrical signal; applying the first electrical signal to a first set of electrodes secured to a first set of positions on the patient; and applying the second electrical signal to a second set of electrodes secured to a second set of positions on the patient. The first electrical signal is a periodic signal of a first frequency. The second electrical signal is a periodic signal of a second frequency. The first frequency and the second frequency differ by a non-zero frequency difference. Providing the first signal to the first electrodes and the second signal to the second electrodes excites a selected set of motor neurons of the patient.

According to yet another aspect of the present invention, a computer program product is provided. In an example embodiment, the computer program product comprises at least one non-transitory computer-readable storage medium having computer-executable program code instructions stored therein. The computer-executable program code instructions comprise program code instructions configured to, when executed by a controller cause a first signal generator to generate a first electrical signal; and cause a second signal generator to generate a second electrical signal. The first electrical signal is applied to a first set of electrodes secured to a first set of positions on the patient. The second electrical signal is applied to a second set of electrodes secured to a second set of positions on the patient. The first electrical signal is a periodic signal of a first frequency. The second electrical signal is a periodic signal of a second frequency. The first frequency and the second frequency differ by a frequency difference. Providing the first signal to the first electrodes and the second signal to the second electrodes excites a selected set of motor neurons of the patient.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 5:
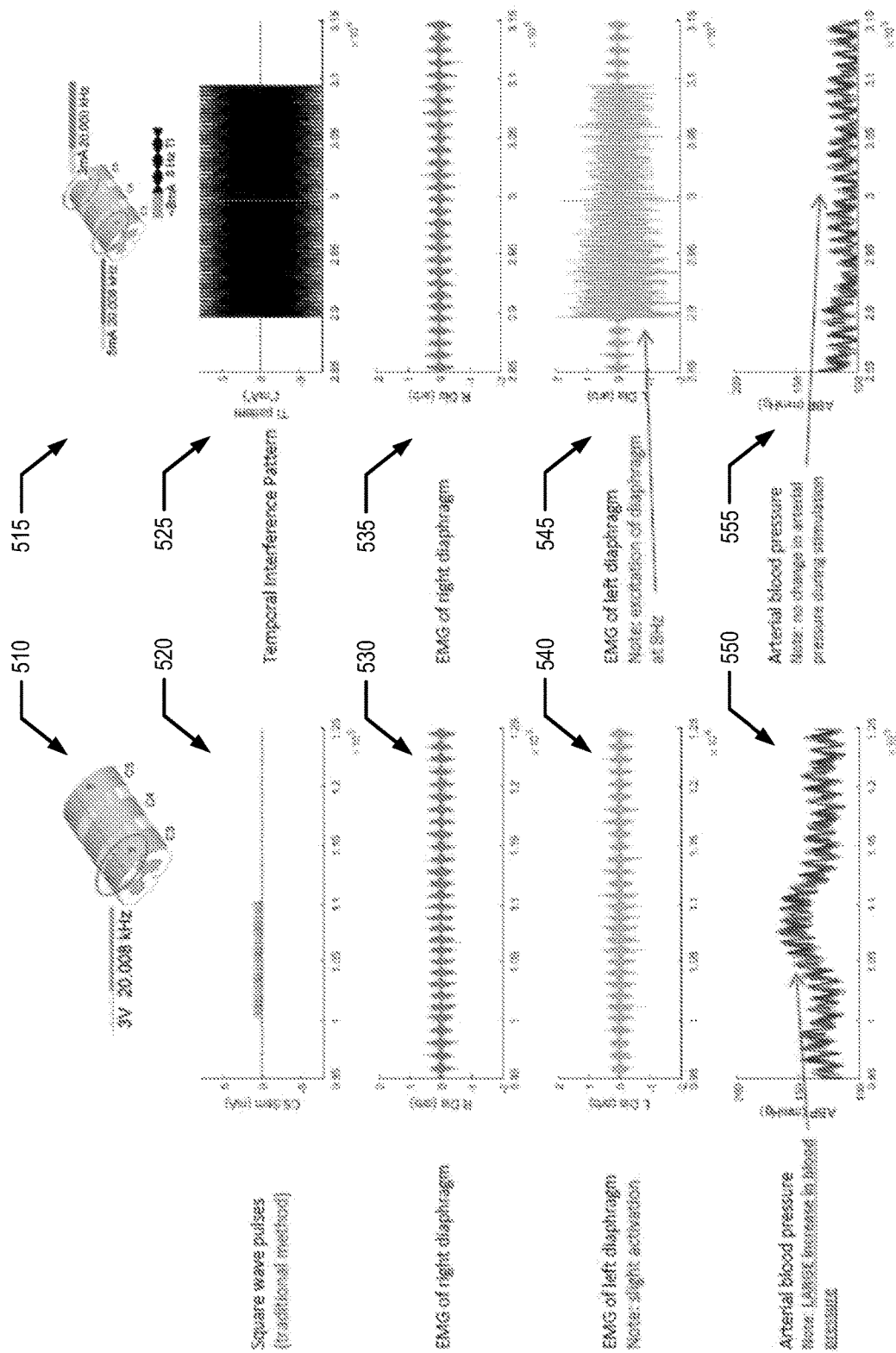

FIG. 5 compares various aspects and experimental data of a first example embodiment to a second control set up.

Figure 6:
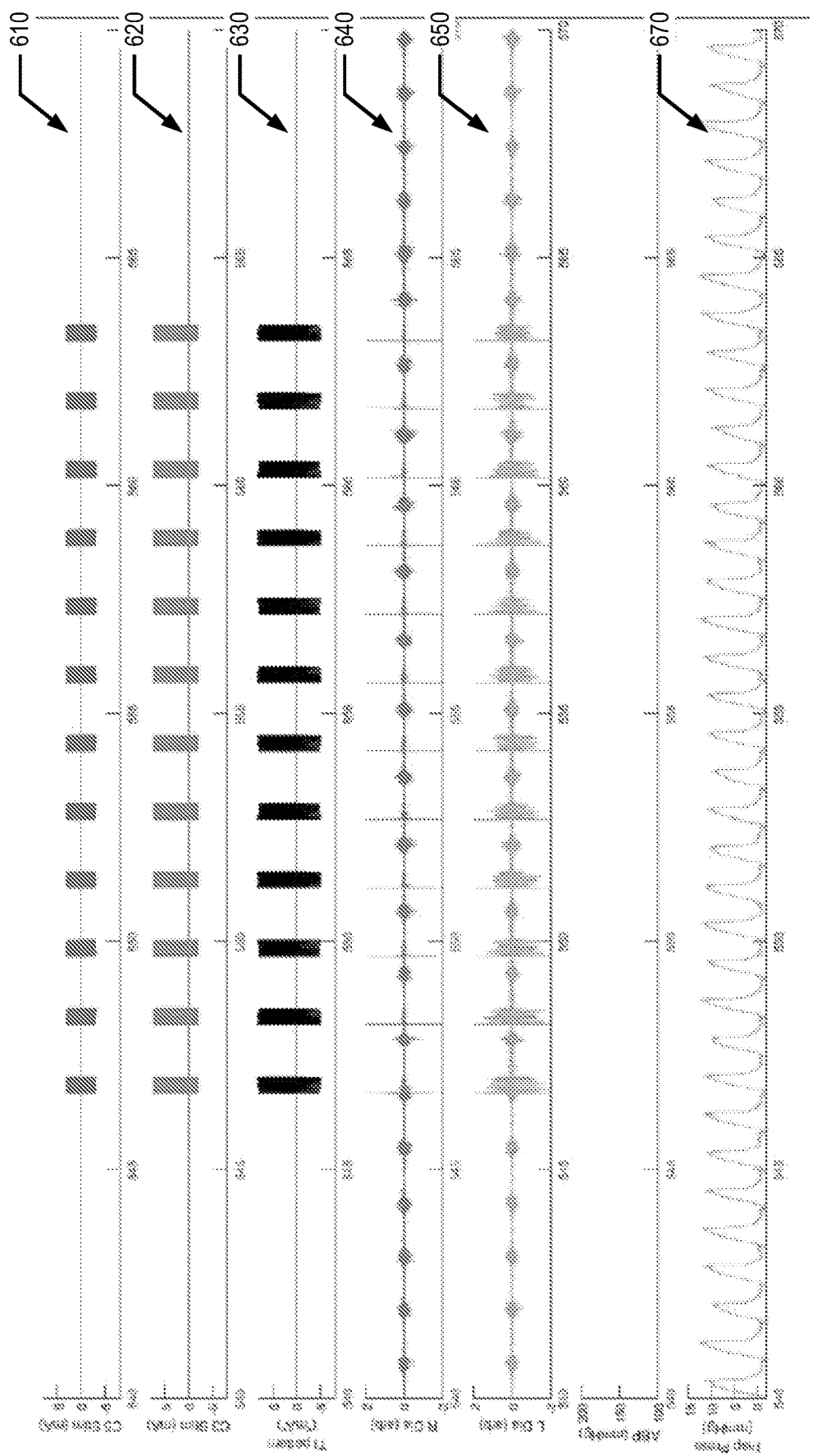

FIG. 6 illustrates experimental data of an embodiment of the present invention, wherein the first and second electrical signals are pulsed.

Figure 7:
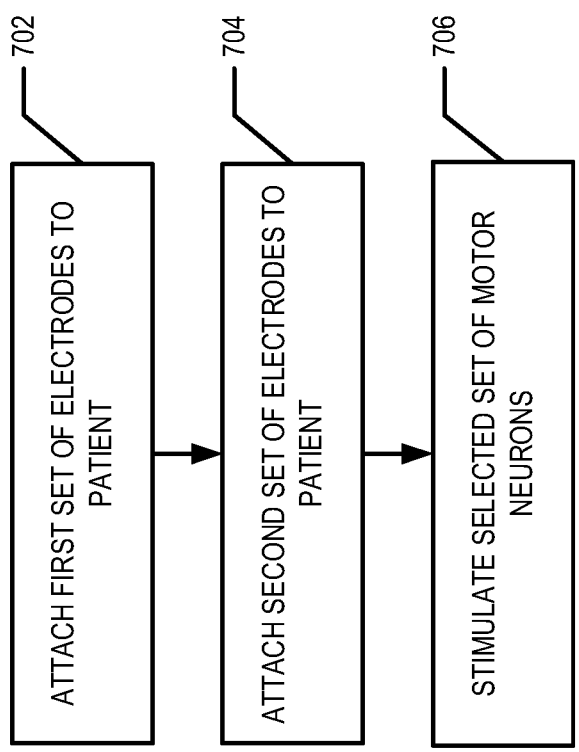

FIG. 7 provides a flowchart illustrating various process and procedures performed, for example, by the system illustrated in FIG. 1, according to an example embodiment.

DETAILED DESCRIPTION OF SOME EXAMPLE EMBODIMENTS

The present invention now will be described more fully hereinafter with reference to the accompanying drawings, in which some, but not all embodiments of the invention or inventions are shown. Indeed, these inventions may be embodied in many different forms and should not be construed as limited to the embodiments set forth herein; rather, these embodiments are provided so that this disclosure will satisfy applicable legal requirements. The term "or" (also designated as"/") is used herein in both the alternative and conjunctive sense, unless otherwise indicated. The terms "illustrative" and "exemplary" are used to be examples with no indication of quality level. As used herein, the terms "approximately" and "generally" refer to within manufacturing and/or engineering tolerances for the corresponding materials and/or elements, unless otherwise indicated. Like numbers refer to like elements throughout.

In an example embodiment, a first electrical signal is applied to a first set of electrodes secured to a first set/pair of positions on a patient and a second electrical signal is applied to a second set of electrodes secured to a second set/pair of positions on the patient. For example, each electrode of the first set of electrodes is secured to a corresponding position of the first set/pair of positions. Similarly, each electrode of the second set of electrodes is secured to a corresponding position of the second set/pair of positions. The first electrical signal and the second electrical signal are periodic electrical signals. For example, the first electrical signal and the second electrical signal may be sine wave signals. The first electrical signal is characterized by a first frequency and the second electrical signal is characterized by a second frequency. The first frequency and the second frequency correspond to the periodicity of the corresponding electrical signal. The first frequency and the second frequency are different frequencies with a frequency difference in the range of 1 Hz to 100 Hz. For example, the first frequency may be 20,008 Hz and the second frequency may be 20,000 Hz. In another example, the first frequency may be 20,050 Hz and the second frequency may be 20,000 Hz. For example, the first and second frequencies may both be greater than 1 kHz.

In an example embodiment, the temporal interference pattern generated by the interference of the first and second electrical signals within the patient's body excites the selected set of motor neurons at the frequency of the temporal interference pattern (e.g., at the frequency difference between the first and second electrical signals). In an example embodiment, the first and second electrical signals may be pulsed. For example, in an example embodiment, pulsing the first and second electrical signals comprises applying the first and second electrical signals for a first length of time (e.g., a time in the range of 100 milliseconds (ms) to 2 seconds, such as approximately 350 ms), followed by not applying the first and second electrical signals for a second length of time (e.g., a time in the range of 100 ms to 3 seconds, such as approximately 1250 ms) and then repeating the application and non-application of the first and second electrical signals to excite the selected set of motor neurons in a pulsed manner Various aspects of the present invention will now be described in more detail.

I. EXEMPLARY SYSTEM ARCHITECTURE

Figure 1A:
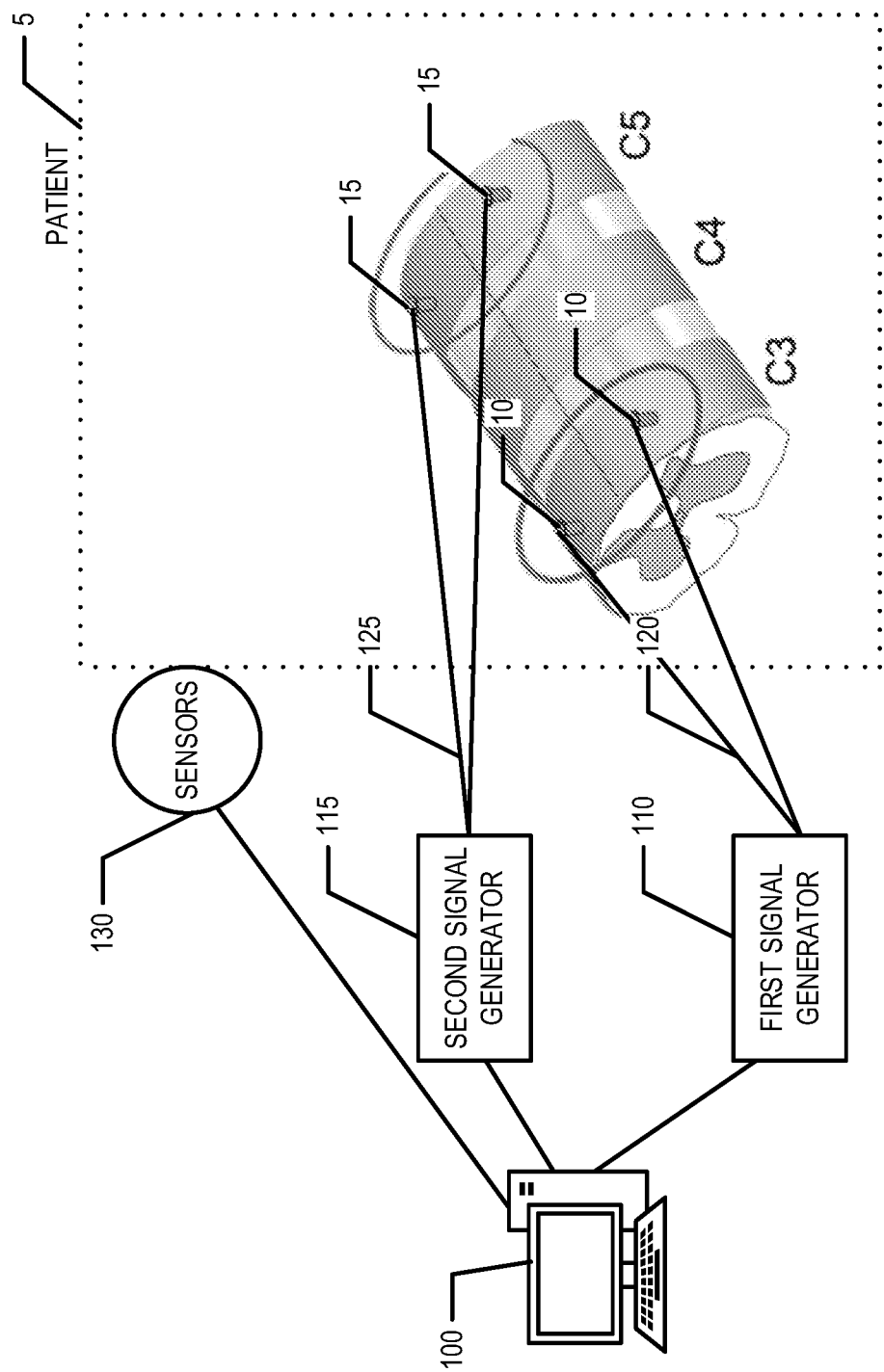
FIG. 1A is a diagram of a system that can be used to practice various embodiments of the present invention.

FIG. 1A provides an illustration of a system that can be used in conjunction with various embodiments of the present invention. As shown in FIG. 1A, the system may include a controller 100, a first signal generator 110, and a second signal generator 115. The first signal generator 110 is in electrical communication with a first set of electrodes 10 via a first set of wires 120. The second signal generator is in electrical communication with a second set of electrodes 15 via a second set of wires 125. The first set of electrodes 10 are positioned and/or secured at a first set/pair of positions on a patient 5 and the second set of electrodes 15 are positioned and/or secured at a second set/pair of positions on the patient 5. In an example embodiment, the first set/pair of positions and the second set/pair of positions are located on the patient's 5 spine. For example, the first set/pair of positions is located at the C3 vertebra and the second set/pair of positions is located at the C5 vertebra, in an example embodiment. For example, in an example embodiment, the first and second sets of electrodes 10, 15 are surgically implanted at the first and second sets/pairs of positions, respectively, via a method known in the art. In an example embodiment, one or more sensors 130 may be attached and/or secured to the patient's body such that excitation of one or more targeted muscles of the patient 5 may be monitored. In an example embodiment, the one or more sensors 130 are in communication with the controller 100 such that the controller 100 may monitor the signals provided by the one or more sensors 130 to monitor the excitation of the one or more targeted muscles of the patient 5. In an example embodiment, the one or more sensors 130 are in communication with another computing entity (in addition to or instead of the controller 100).

Figure 1B:
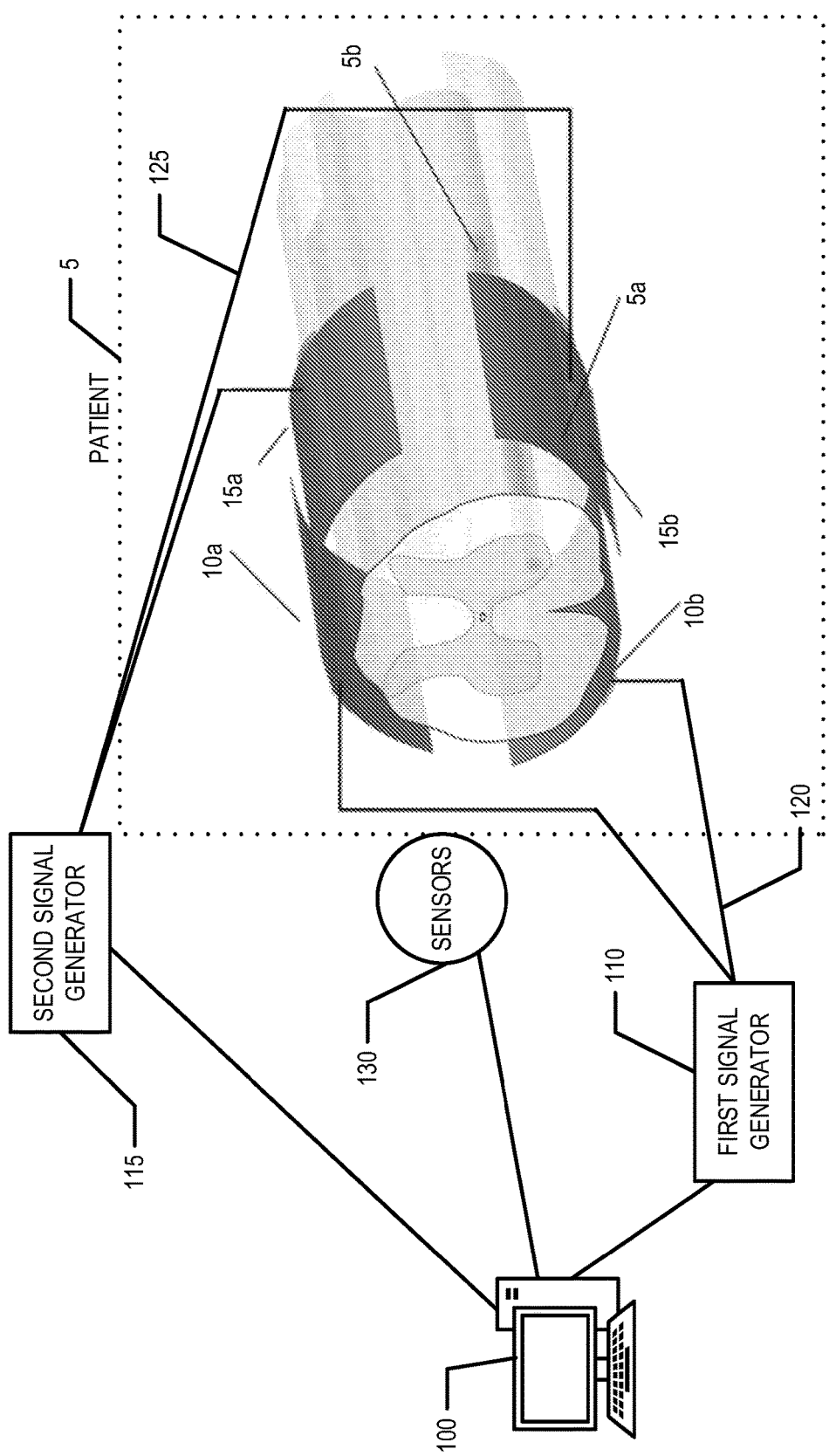
FIG. 1B is a diagram of another system that can be used to practice various embodiments of the present invention.

FIG. 1B provides an illustration of another system that can be used in conjunction with various embodiments of the present invention. As shown in FIG. 1B, the system may include a controller 100, a first signal generator 110, and a second signal generator 115. The first signal generator 110 is in electrical communication with a first set of electrodes 10a and 10b via a first set of wires 120. The second signal generator is in electrical communication with a second set of electrodes 15a and 15b via a second set of wires 125. The first set of electrodes 10a and 10b are secured at a first set/pair of positions and the second set of electrodes 15a and 15b are secured at a second set/pair of positions on the patient's body. In various embodiments, electrodes 10a and 15a are disposed on the patient's 5 dorsal surface to provide transcutaneous stimulation and/or are subcutaneously positioned proximate the patient's 5 dorsal surface to provide subcutaneous stimulation. In various embodiments, electrodes 10b and 15b are disposed on the patient's 5 ventral surface to provide transcutaneous stimulation and/or are subcutaneously positioned proximate the patient's 5 ventral surface to provide subcutaneous stimulation. The electrodes 10a, 10b, 15a, and 15b are positioned and/or secured at positions on a patient 5 that are exterior to the patient's vertebral bones, muscles, and/or skin 5a and in the vicinity of the patient's phrenic motor pool 5b. In an example embodiment, the electrodes 10a, 10b, 15a, and 15b are positioned proximate the patient's 5 C3 vertebra and/or C5 vertebra. For example, the electrodes 10, 15 may be surgically implanted such that they are secured to the patient's spine and/or via an epidural. In an example embodiment, one or more sensors 130 may be attached and/or secured to the patient's body such that excitation of one or more targeted muscles of the patient 5 may be monitored. In an example embodiment, the one or more sensors 130 are in communication with the controller 100 such that the controller 100 may monitor the signals provided by the one or more sensors 130 to monitor the excitation of the one or more targeted muscles of the patient 5. In an example embodiment, the one or more sensors 130 are in communication with another computing entity (in addition to or instead of the controller 100).

Additionally, while FIGS. 1A and 1B illustrates certain system entities as separate, standalone entities, the various embodiments are not limited to this particular architecture. For example, the first and second signal generators 110, 115 may be incorporated into one signal generator that is capable of generating two different electrical signals, in an example embodiment. In another example embodiment, each of the first and second signal generator 110, 115 may have a controller 100 incorporated therein such that an additional controller is not required.

a. Exemplary Controller

Figure 2:
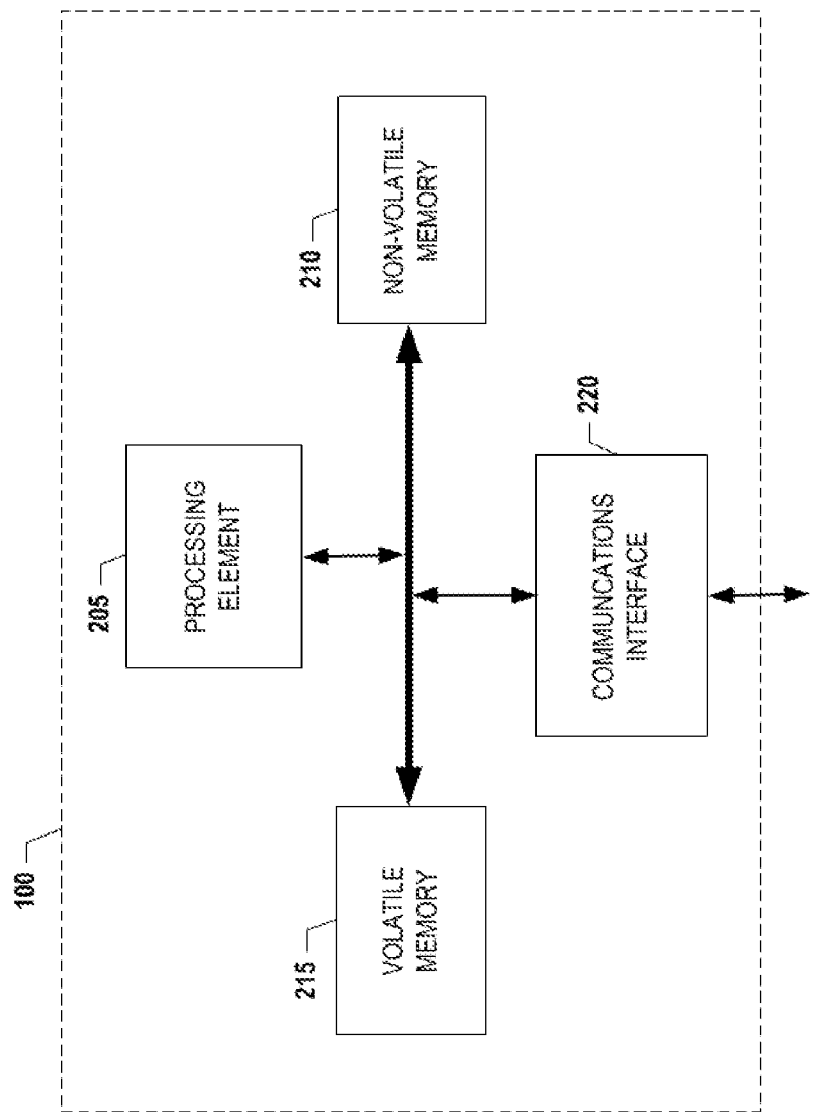
FIG. 2 is a schematic of a controller in accordance with certain embodiments of the present invention.

FIG. 2 provides a schematic of a controller 100 according to one embodiment of the present invention. In general, controller 100 is a computing entity configured to control at least one of the first and second signal generators 110, 115, monitor signals provided by the one or more sensors 130, and/or the like. In general, the terms computing entity, entity, device, system, and/or similar words used herein interchangeably may refer to, for example, one or more computers, computing entities, desktop computers, mobile devices, mobile phones, tablets, phablets, notebooks, laptops, distributed systems, smart wearable items/devices, processing devices, processing entities, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As shown in FIG. 2, in one embodiment, the controller 100 may include or be in communication with one or more processing elements 205 (also referred to as processors, processing circuitry, and/or similar terms used herein interchangeably) that communicate with other elements within the controller 100 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the controller 100 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database. For example, the controller 100 may store a database comprising sensor information/data received from the one or more sensors 130, and/or other database(s).

In one embodiment, the controller 100 may further include or be in communication with volatile media (also referred to as volatile storage, memory, memory storage, memory circuitry and/or similar terms used herein interchangeably). In one embodiment, the volatile storage or memory may also include one or more volatile storage or memory media 215 as described above, such as RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 205. Thus, the databases, database instances, database management system entities, data, applications, programs, program modules, scripts, source code, object code, byte code, compiled code, interpreted code, machine code, executable instructions, and/or the like may be used to control certain aspects of the operation of the controller 100 with the assistance of the processing element 205 and operating system.

As indicated, in one embodiment, the controller 100 may also include one or more communications interfaces 220 for communicating with various computing entities, such as by communicating data, content, information, and/or similar terms used herein interchangeably that can be transmitted, received, operated on, processed, displayed, stored, and/or the like. For instance, the controller 100 may communicate with computing entities or communication interfaces of the first signal generator 110, the second signal generator 115, the one or more sensors, one or more computing entities, and/or the like.

Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the controller 100 may be configured to communicate via wireless external communication networks using any of a variety of protocols, such as general packet radio service (GPRS), Universal Mobile Telecommunications System (UMTS), Code Division Multiple Access 2000 (CDMA2000®), CDMA2000 1×(1× RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi®), Wi-Fi Direct®, 802.16 (WiMAX®), ultra wideband (UWB), infrared (IR) protocols, near field communication (NEC) protocols, Wibree®, Bluetooth® protocols, wireless universal serial bus (USB) protocols, and/or any other wireless protocol. The controller 100 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (MAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the controller's 100 components may be located remotely from other controller 100 components, such as in a distributed system. Furthermore, one or more of the components may be combined and additional components performing functions described herein may be included in the controller 100. Thus, the controller 100 can be adapted to accommodate a variety of needs and circumstances.

b. Exemplary Signal Generator

In an example embodiment, each of the first and second signal generators 110, 115, is an electronic device configured for generating a periodic electrical signal. In an example embodiment, the periodic electrical signals generated by the first and second signal generators 110, 115 are sinusoidal. In various embodiments, various periodic electrical signals may be used. In an example embodiment, the first signal generator 110 is configured to generate a periodic electrical signal having a first frequency and the second signal generator 115 is configured to generate a periodic electrical signal having a second frequency. The first and second frequencies are each greater than 1 kHz. For example, in an example embodiment, the first frequency is 20,008 Hz and the second frequency is 20,000 Hz. In another example embodiment, the first frequency is 20,050 Hz and the second frequency is 20,000 Hz. In an example embodiment, the first and second electrical signals may each have amplitudes greater than zero and up to 10 mA. For example, in an example embodiment, each of the first electrical signal and the second electrical signal may have an amplitude in the range of 1 µA-10 mA.

The first and second frequencies are separated by a frequency difference (e.g., the first frequency is not equal to the second frequency). In an example embodiment, the first frequency is higher than the second frequency. In another example embodiment, the second frequency is higher than the first frequency. In an example embodiment, the frequency difference is in the range from 0.1 Hz to 200 Hz. In another exemplary embodiment, the frequency difference may be in the range of 1 Hz to 100 Hz. For example, the frequency difference may be 4 Hz, 8 Hz, 48 Hz, 50 Hz, and/or the like, in various embodiments. In still other embodiments, it should be understood that the frequency difference may also be less than 0.1 Hz or greater than 200 Hz, should that be desirable for a particular application.

In an example embodiment, the first and second signal generators 110, 115 are configured to provide pulsed first and second electrical signals. For example, the first and second signal generators 110, 115 may be configured to provide the first and second electrical signals, respectively, for a first length of time stop providing the first and second electrical signals for a second length of time, and the again provide the first and second electrical signals for the first length of time. In an example embodiment, the first length of time is a stimulation and/or inspiratory period in the range of 100 ms to 2 seconds. In an example embodiment, the first length of time is approximately 350 ms. In an example embodiment, the second length of time is an expiratory period between stimulations in and is in the range of 100 ms to 3 seconds. In an example embodiment, the second length of time is approximately 1250 ms. In an example embodiment, the first and second signal generators 110, 115 are configured to provide continuous first and second electrical signals. In various example embodiments, the first length of time (e.g., the length of time the first and second electrical signals are on or provided) is one third to one fifth the second length of time (e.g., the length of time the first and second electrical signals are off or not provided).

In an example embodiment, the first and second signal generators 110, 115 may generate the first and second signal, respectively, in response to instructions provided by the controller 100. In one example embodiment, each of the first and second signal generators 110, 115 may comprise a controller 100 in addition to or in place of being in communication with an external controller 100.

II. EXEMPLARY SYSTEM OPERATION

In an example embodiment, a patient 5 may have a first set of electrodes attached, positioned, and/or secured to their body at first set/pair of positions and a second set of electrodes attached, positioned, and/or secured to their body at second set/pair of positions. In an example embodiment, the first and second sets/pairs of positions are both along the patient's 5 spinal cord. In an example embodiment, the first and second sets/pairs of positions are on and/or proximate the patient's ventral and dorsal surfaces in the vicinity of the patient's spinal cord (e.g., on the patient's neck, torso, and/or abdominal area). In an example embodiment, the first set/pair of positions are on the patient's 5 C3 vertebra and the second set/pair of positions are on the patient's 5 C5 vertebra. For example, in at least one embodiment, wherein the selected set of motor neurons correspond to the patient's diaphragm, the first electrical signal may be applied to the patient's C3 vertebra and the second electrical signal may be applied to the patient's C5 vertebra. For various other selected sets of motor neurons, different positions on the patient's 5 body may be used for application of the first and second electrical signals. As should be understood, various motor neurons may be excited via application of the first and second electrical signals to the first and second electrodes, respectively, based on the first set/pair of positions and the second set/pair of positions. For example, the set of motor neurons that are excited via application of the first and second electrical signals to the first and second electrodes, respectively, may be selected based on the where on the patient's body the first and second set/pair of positions are located. In an example embodiment, wherein the first set/pair of positions are on the patient's 5 C3 vertebra and the second set/pair of positions are on the patient's 5 C5 vertebra, the selected set of motor neurons for excitation may correspond to the patient's 5 diaphragm. In an example embodiment, the electrodes 10a, 10b, 15a, 15b may be positioned on the patient's skin and/or subcutaneously on or just beneath the patient's ventral surface (10b, 15b) and/or dorsal surface (10a, 15a) in the vicinity of the patient's phrenic motor pool 5b. Sets of motor neurons corresponding to various muscles may be selected for excitation and the location of the first and second sets/pairs of positions may be determined accordingly. For example, the electrodes 10, 15 and/or 10a, 10b, 15a, 15b may be disposed proximate the motor pool corresponding to the muscle targeted for excitation.

The controller 100 controls the first signal generator 110 and the second signal generator 115 to each provide a periodic electrical signal. In an example embodiment, the controller 100 comprises a real time clock or other clock (e.g., processor clock) configured to cause the first and second signal generators 110, 115 to provide the first and second electrical signals simultaneously or at approximately the same time. The first electrical signal is provided by the first signal generator 110 to the first set of wires 120. The first set of wires 120 in turn provides the first electrical signal to the first set of electrodes 10 (e.g., 10a, 10b) positioned and/or secured to the patient's 5 body at first set/pair of positions (e.g., on and/or just below the patient's ventral and dorsal surfaces proximate the motor pool corresponding to the muscle targeted for excitation). The second signal is provided by the second signal generator 115 to the second set of wires 125. The second set of wires 125 in turn provides the second electrical signal to the second set of electrodes 15 (e.g., 15a, 15b) positioned and/or secured to the patient's 5 body at second set/pair of positions (e.g., on and/or just below the patient's ventral and dorsal surfaces proximate the motor pool corresponding to the muscle targeted for excitation).

The first and second electrical signals are periodic electrical signals characterized by a first frequency and a second frequency, respectively. The first frequency and the second frequency are separated by a frequency difference in the range of 0.1 to 200 Hz. For example, the frequency difference may be in the range of 1 Hz to 100 Hz in one non-limiting and exemplary embodiment. For example, the first frequency may be 20,008 Hz or 20,050 Hz and the second frequency may be 20,000 Hz. Thus, the first and second electrical signal may interfere with one another within the patient's body (e.g., in the vicinity of and/or in an area between the first set/pair of positions and the second set/pair of positions) to generate a temporal interference pattern having a periodicity of the frequency difference between the first and second electrical signals. A set of motor neurons located in the vicinity of and/or in an area between the first set/pair of positions and the second set/pair of positions may be excited by the temporal interference pattern. In an example embodiment, the set of motor neurons may be excited at a frequency equal to and/or approximately the frequency difference. As a result of exciting the set of motor neurons, the muscle(s) corresponding to the motor neurons may also be excited and/or activated.

Example Experimental Data

Figure 3:
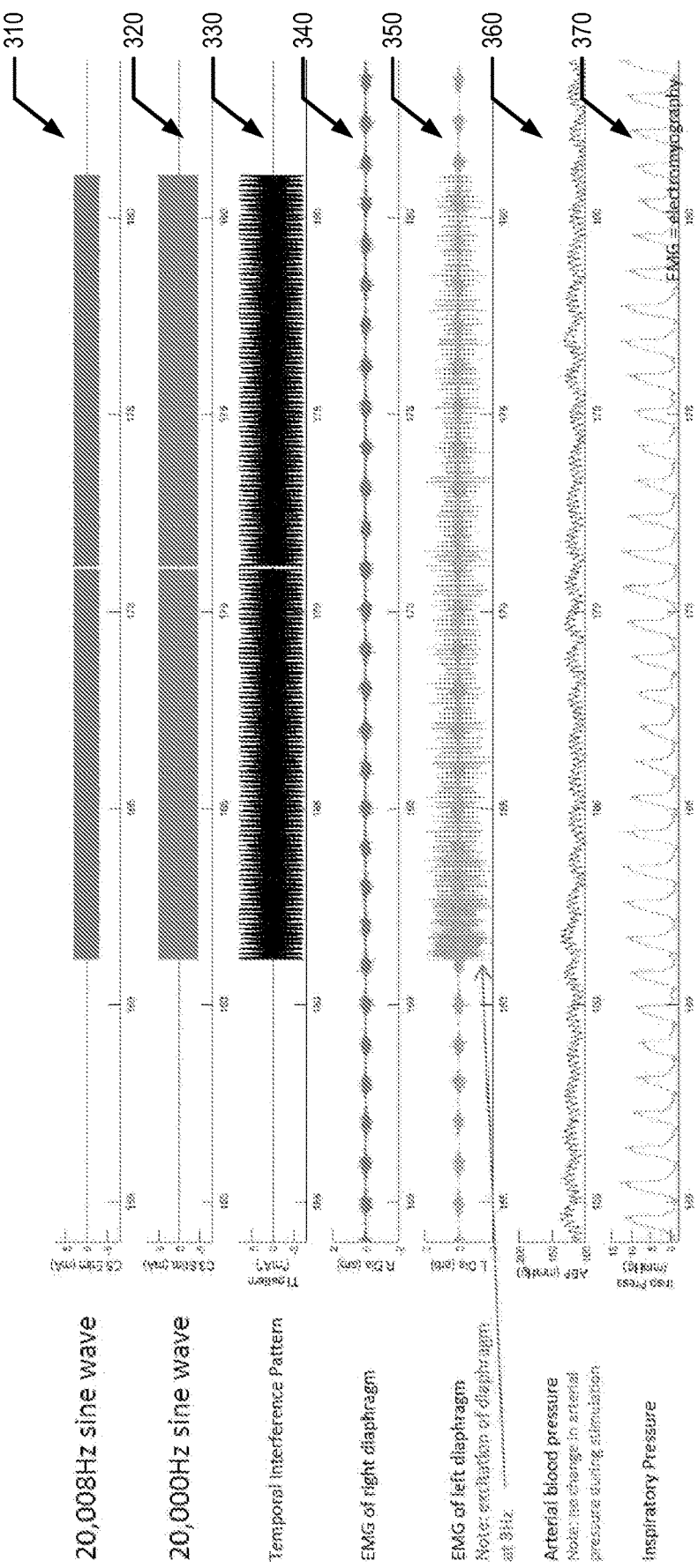
FIG. 3 illustrates experimental data of applying a first electrical signal to a first set of electrodes secured to the patient at a first set/pair of positions and a second electrical signal to a second set of electrodes secured to the patient at a second set/pair of positions, in accordance with an embodiment of the present invention.

FIG. 3 illustrates experimental data captured using a first example embodiment. For the collection of the experimental data, the patient 5 is a spinally intact, ventilated vagotomized animal (e.g., a rat). In the first example embodiment, the first signal has a frequency of 20,008 Hz and an amplitude of 3 mA and the second signal has a frequency of 20,000 Hz and an amplitude of 5 mA. The temporal interference pattern has a frequency of 8 Hz and approximately 8 mA. The first and second electrical signals are sine waves in the first example embodiment. The first set/pair of positions is the C3 vertebra and the second set/pair of positions is the C5 vertebra in the first example embodiment.

Line 310 of FIG. 3 shows the first signal being applied to the first set of electrodes 120, line 320 shows the second signal being applied to the second set of electrodes 125, and line 330 shows the temporal interference pattern generated by the first and second signals. Line 340 shows an electromyography (EMG) of the right diaphragm of the patient 5, line 350 shows an EMG of the left diaphragm of the patient 5, line 360 shows the arterial blood pressure of the patient 5, and line 370 shows the inspiratory pressure of the patient 5. For example, the EMG of the right diaphragm, EMG of the left diaphragm, arterial blood pressure, and inspiratory pressure of the patient 5 may be captured using the one or more sensors 130. As can be seen from FIG. 3, in the first example embodiment the left diaphragm of the patient 5 was excited at a frequency of 8 Hz, matching the periodicity of the temporal interference pattern. Additionally of note, the arterial blood pressure of the patient 5 did not change when the first and second signals were applied.

Figure 4:
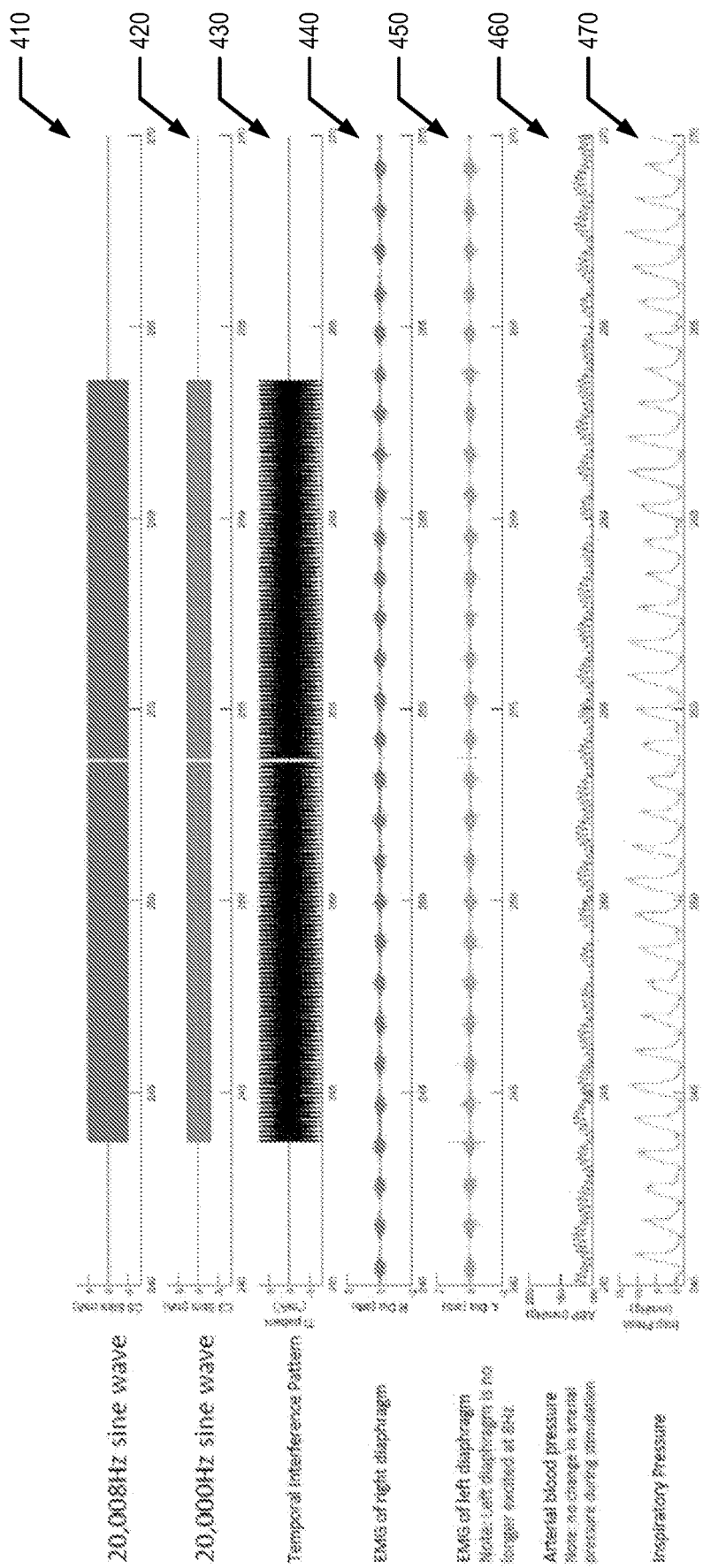
FIG. 4 illustrates experimental data of a first control set up.

FIG. 4 illustrates experimental data captured using a first control set up. In the first control set up, the patient 5 is again a spinally intact, ventilated vagotomized animal (e.g., a rat). In the first control set up, the first signal has a frequency of 20,008 Hz and an amplitude of 5 mA and the second signal has a frequency of 20,000 Hz and an amplitude of 3 mA. The temporal interference pattern has a frequency of 8 Hz and approximately 8 mA. The first and second electrical signals are sine waves in the first control set up. The first set/pair of positions is the C3 vertebra and the second set/pair of positions is the C5 vertebra in the first control set up. The first control set up is similar to the first example embodiment, but with the amplitudes of the first and second electrical signals switched.

Line 410 of FIG. 4 shows the first signal being applied to the first set of electrodes 120, line 420 shows the second signal being applied to the second set of electrodes 125, and line 330 shows the temporal interference pattern generated by the first and second signals. Line 440 shows an EMG of the right diaphragm of the patient 5, line 450 shows an EMG of the left diaphragm of the patient 5, line 460 shows the arterial blood pressure of the patient 5, and line 470 shows the inspiratory pressure of the patient 5. As can be seen from FIG. 4, in the first control set up, the left diaphragm of the patient 5 was not excited. In particular, by switching the amplitudes of the first and second electrical signals with respect to the first example embodiment, the location of maximal interference is shifted out of the diaphragm motor pool, resulting in the motor neurons corresponding to the patient's 5 diaphragm not being excited.

FIG. 5 provides a comparison between the first example embodiment and a second control set up. In the second control set up, the patient 5 is again a spinally intact, ventilated vagotomized animal (e.g., a rat). In the second control set up, a single electrical signal having a frequency of 20,008 Hz and amplitude of 3 mA is applied to the C3 vertebra of the patient 5, as shown by diagram 510. Diagram 515 shows that in the first example embodiment, the first electrical signal has a frequency of 20,008 Hz, an amplitude of 3 mA, and is applied to electrodes secured to the C3 vertebra of the patient 5 while the second electrical signal has a frequency of 20,000 Hz, an amplitude of 5 mA, and is applied to the C5 vertebra of the patient 5. Thus, in the first example embodiment, a temporal interference pattern having a periodicity of 8 Hz and an amplitude of approximately 8 mA is generated. Line 520 illustrates the single electrical signal input in the second control set up and line 525 illustrates the temporal interference pattern of the first example embodiment. Line 530 shows an EMG of the right diaphragm when the signal of line 520 is applied to the electrodes secured to the C3 vertebra of the patient 5. Line 535 shows an EMG of the right diaphragm when the temporal interference pattern of line 525 is applied to the patient 5 (e.g., via the first signal being applied to the first electrodes secured to the patient's C3 vertebra and the second signal being applied to the second electrodes secured to the patient's C5 vertebra). Line 540 shows an EMG of the patient's 5 left diaphragm when the signal of line 520 is applied to the electrodes secured to the C3 vertebra of the patient 5. Line 545 shows an EMG of the patient's 5 left diaphragm when the temporal interference pattern of line 525 is applied to the patient 5 (e.g., via the first signal being applied to the first electrodes secured to the patient's C3 vertebra and the second signal being applied to the second electrodes secured to the patient's C5 vertebra). As shown at line 540, a slight excitation of the left diaphragm is observed in the second control setup, but this excitation is considerably less than the excitation of the left diaphragm observed in the first example embodiment. Line 550 shows the arterial blood pressure of the patient 5 when the signal of line 520 is applied to the electrodes secured to the C3 vertebra of the patient 5. Line 555 shows the patient's 5 arterial blood pressure when the temporal interference pattern of line 525 is applied to the patient 5 (e.g., via the first signal being applied to the first electrodes secured to the patient's C3 vertebra and the second signal being applied to the second electrodes secured to the patient's C5 vertebra). As evident in line 550, a significant increase of the patient's arterial blood pressure is measured in the second control set up when the signal is applied to the electrodes secured to the C3 vertebra of the patient 5, while the patient's arterial blood pressure does not change when temporal interference pattern of line 525 is applied to the patient in the first example embodiment.

FIG. 6 illustrates experimental data captured using a second example embodiment. For the collection of the experimental data, the patient 5 is a spinally intact, ventilated vagotomized animal (e.g., a rat). In the second example embodiment, the first signal has a frequency of 20,050 Hz and an amplitude of 3 mA and the second signal has a frequency of 20,000 Hz and an amplitude of 5 mA. The temporal interference pattern has a frequency of 50 Hz and approximately 8 mA. The first and second electrical signals are sine waves in the second example embodiment. The first set/pair of positions is the C3 vertebra and the second set/pair of positions is the C5 vertebra in the first example embodiment. The first and second electrical signals are pulsed. For example, the first and second electrical signals are provided to the first and second set of electrodes, respectively, for a first length of time (e.g., approximately 350 ms) and then not provided for a second length of time (e.g., approximately 1250 ms).

Line 610 of FIG. 6 shows the first signal being applied to the first set of electrodes 120, line 620 shows the second signal being applied to the second set of electrodes 125, and line 630 shows the temporal interference pattern generated by the first and second signals. Line 640 shows an EMG of the right diaphragm of the patient 5, line 650 shows an EMG of the left diaphragm of the patient 5, and line 370 shows the inspiratory pressure of the patient 5. For example, the EMG of the right diaphragm, EMG of the left diaphragm, arterial blood pressure, and inspiratory pressure of the patient 5 may be captured using the one or more sensors 130. As can be seen from FIG. 6, in the second example embodiment, the left and right diaphragms of the patient 5 were excited at a frequency of 50 Hz, matching the periodicity of the temporal interference pattern, when the first and second signals were being applied. The left and right diaphragms were not excited during the time periods where the first and second signals were not being applied. Additionally of note, the arterial blood pressure of the patient 5 did not change when the first and second signals were applied.

As should be understood, various embodiments may cause activation of the patient's 5 diaphragm such that a patient with a paralyzed diaphragm may be removed from a ventilator, at least for short periods of time. In an example embodiment, the controller 100, first signal generator 110, and the second signal generator 115 may be manufactured into device or housing small enough for easy use in various mobile applications. For example, the device may be disposed, placed, and/or secured in a wheelchair and/or the like for easy use with a patient positioned in the wheelchair. In various embodiments, various muscles, may be activated and/or excited based on the placement of the first and second electrodes 10, 15.

Method of Use

FIG. 7 illustrates a flowchart of various processes and procedures that may be performed in accordance with an example embodiment. At block 702, the first set of electrodes 10 are attached to the patient 5. For example, the first set of electrodes 10 (e.g., 10a, 10b) may be attached to the patient 5 at the first set/pair of positions. For example, the first set of electrodes 10 may be attached on the patient's skin (e.g., ventral and/or dorsal surface), subcutaneously (e.g., just beneath the patient's ventral and/or dorsal surface), and/or on one or more vertebra of the patient's spine (e.g., the C3 vertebra via, for example, an epidural). At block 704 the second set 15 of electrodes are attached to the patient 5. For example, the second set of electrodes 15 (e.g., 15a, 15b) may be attached to the patient 5 at the second set/pair of positions. For example, the second set of electrodes 15 may be attached on the patient's skin (e.g., ventral and/or dorsal surface), subcutaneously (e.g., just beneath the patient's ventral and/or dorsal surface), and/or on one or more vertebra of the patient's spine (e.g., the C5 vertebra via, for example, an epidural).

At block 706, after placement of the electrodes on the patient's skin (e.g., ventral and/or dorsal surface), subcutaneously (e.g., just beneath the patient's ventral and/or dorsal surface), and/or on one or more vertebra of the patient's spine (e.g., the C3 and C5 vertebra), the selected set of motor neurons is stimulated. For example, the first signal generator 110 is caused to generate the first electrical signal. For example, the controller 100 may cause and/or instruct the first signal generator 110 to generate the first electrical signal at the first frequency and at a first amplitude. For example, the first electrical signal may be a periodic signal characterized by the first frequency and the first amplitude. The first electrical signal is applied to the first set of electrodes 10 (e.g., 10a, 10b) secured to first set/pair of positions on the patient 5. For example, the first set of wires 120 may provide the first electrical signal to the first set of electrodes 10 (e.g., 10a, 10b) from the first signal generator 110. Additionally, the second signal generator 115 is caused to generate the second electrical signal. For example, the controller 100 may cause and/or instruct the second signal generator 115 to generate the second electrical signal at the second frequency and at a second amplitude. For example, the second electrical signal may be a periodic signal characterized by the second frequency and the second amplitude. In an example embodiment, the first electrical signal and the second electrical signal are generated by the corresponding signal generators simultaneously and/or approximately at the same time. The second electrical signal is applied to the second set of electrodes 15 (e.g., 15a, 15b) secured to the second set/pair of positions on the patient 5. For example, the second set of wires 125 may provide the second electrical signal to the second set of electrodes 15 from the second signal generator 115. In an example embodiment, the first electrical signal is applied to the first set of electrodes 10 and the second electrical signal is applied to the second set of electrodes 15 simultaneously and/or approximately at the same time.

In at least one non-limiting and exemplary embodiment, the first and second frequency differ by a frequency difference that is in the range of 0.1 Hz to 200 Hz. In an example embodiment, the first and second frequency differ by a frequency difference that is in the range of 1 Hz to 100 Hz. In an example embodiment, providing the first signal to the first electrodes and the second signal to the second electrodes excites a selected set of motor neurons of the patient. In an example embodiment, the first and second electrical signals are provided in a pulsed manner such that the first and second signals are applied to the first and second electrodes, respectively, for a first length of time, then not applied for a second length of time, and then applied again in a repetitive manner Thus, the selected set of motor neurons may be stimulated.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution. For example, a software component may be configured to cause the controller 100 to control the first and second signal generators 110, 115 to provide the first and second signals in accordance with an example embodiment, monitor signals provided by the one or more sensors 130, provide alerts and/or notifications based on the monitoring of the signals provided by the one or more sensors 130, and/or the like.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD™), Blu-ray® disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps. Appendices A, B, and C provide additional information regarding various embodiments of the present invention.

IV. CONCLUSION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A system for exciting a selected set of motor neurons of a patient, the system comprising:
   one or more signal generators configured for generating a first electrical signal and a second electrical signal;
   a first set of wires configured to provide the first electrical signal to a first set of electrodes, wherein the first set of electrodes are configured for being secured to a first set of positions on the patient proximate a C3 vertebra of the patient;
   a second set of wires configured to provide the second electrical signal to a second set of electrodes, wherein the second set of electrodes are configured for being secured to a second set of positions on the patient proximate a C5 vertebra of the patient; and
   a controller configured to control operation of the one or more signal generators such that:
   the first electrical signal is provided to the first set of electrodes, wherein the first electrical signal is a periodic signal of a first frequency,
   the second electrical signal is provided to the second set of electrodes, wherein the second electrical signal is a periodic signal of a second frequency,
   the first frequency and the second frequency differ by a non-zero frequency difference that produces a temporal interference pattern between the first frequency and the second frequency, and
   wherein the first signal provided to the first electrodes and the second signal provided to the second electrodes for exciting the set of motor neurons of the patient causing excitation of a diaphragm of the patient.

2. The system of claim 1, wherein the first frequency is greater than 1 kHz and the second frequency is greater than 1 kHz.

3. The system of claim 1, wherein the first set of positions and the second set of positions are located on the patient's surface or skin.

4. The system of claim 3, wherein each of the first set of positions and the second set of positions are on or proximate one of the patient's ventral or dorsal surface.

5. The system of claim 1, wherein the first set of positions and the second set of positions are subcutaneous positions.

6. The system of any of claim 1, wherein the first signal and the second signal are pulsed signals.

7. The system of claim 6, wherein a pulse of the first and second signals comprises the first and second signal being provided for a first length of time followed by the first and second signals being off for a second length of time, the first length of time being in the range of 100 milliseconds to 2 seconds and the second length of time being in the range of 100 milliseconds to 3 seconds.

8. The system of any of claim 1, wherein the motor neurons are associated with the patient's diaphragm and providing the first signal to the first electrodes and the second signal to the second electrodes excites the patient's diaphragm.

9. The system of claim 8, wherein the patient's diaphragm muscle is paralyzed, following neurologic injury, or rendered inactive due to drug overdose.

10. The system of any of claim 1, wherein the first signal has an amplitude of 3 mA and the second signal has an amplitude of 5 mA.

11. The system of any of claim 1, wherein the frequency difference is approximately 50 Hz.

12. The system of any of claim 1, wherein the controller comprises a processor or microprocessor configured to act as a clock for controlling the first signal generator to generate the first signal and the second signal generator to generate the second signal.

13. The system of any of claim 1, wherein at least one of the first set of positions and the second set of positions are located on or near the patient's spinal cord.

14. The system of any of claim 1, wherein excitation of the motor neurons causes excitation of one or more muscles of the patient.

15. The system of any of claim 1, wherein the first frequency is about 20,000 Hz and the frequency difference being in the range of 0.1 to 200 Hz.

16. The system of claim 1, wherein the first set of electrodes are configured to be secured subcutaneously proximate the C3 vertebra of the patient and the second set of electrodes are configured to be secured subcutaneously proximate the C5 vertebra of the patient.

17. A method for exciting a selected set of motor neurons of a patient, the method comprising:
    causing a first signal generator to generate a first electrical signal;
    causing a second signal generator to generate a second electrical signal;
    applying the first electrical signal to a first set of electrodes secured to a first set of positions on the patient proximate a C3 vertebra of the patient; and
    applying the second electrical signal to a second set of electrodes secured to a second set of positions on the patient proximate a C5 vertebra of the patient,
    wherein:
        the first electrical signal is a periodic signal of a first frequency,
        the second electrical signal is a periodic signal of a second frequency,
        the first frequency and the second frequency differ by a non-zero frequency difference that produces a temporal interference pattern between the first frequency and the second frequency, and
        wherein providing the first signal to the first electrodes and the second signal to the second electrodes excites a selected set of motor neurons of the patient causing excitation of a diaphragm of the patient.

18. The method of claim 17, wherein the first frequency is greater than 1 kHz and the second frequency is greater than 1 kHz.

19. The method of claim 17, wherein the first set of positions and the second set of positions are located on the patient's surface or skin.

20. The method of claim 19, wherein each of the first set of positions and the second set of positions are on or proximate one of the patient's ventral or dorsal surface.

21. The method of claim 17, wherein the first set of positions and the second set of positions are subcutaneous positions.

22. The method of any of claim 17, wherein the first signal and the second signal are pulsed signals.

23. The method of claim 22, wherein a pulse of the first and second signals comprises the first and second signal being provided for a first length of time followed by the first and second signals being off for a second length of time, the first length of time being in the range of 100 milliseconds to 2 seconds and the second length of time being in the range of 100 milliseconds to 3 seconds.

24. The method of any of claim 17, wherein the motor neurons are associated with the patient's diaphragm and providing the first signal to the first electrodes and the second signal to the second electrodes excites the patient's diaphragm.

25. The method of claim 24, wherein the patient's diaphragm muscle is paralyzed or rendered inactive due to drug overdose.

26. The method of any of claim 17, wherein the first signal has an amplitude of 5 mA and the second signal has an amplitude of 3 mA.

27. The method of any of claim 17, wherein the frequency difference is approximately 50 Hz.

28. The method of any of claim 17, wherein generation of the first signal by the first signal generator and generation of the second signal by the second signal generator are controlled by a controller.

29. The method of claim 28, wherein the controller comprises a processor or microprocessor configured to act as a clock for controlling the first signal generator to generate the first signal and the second signal generator to generate the second signal.

30. The method of any of claim 17, wherein at least one of the first set/pair of positions and the second set/pair of positions are located on the patient's spinal cord.

31. The method of any of claim 17, wherein excitation of the motor neurons causes excitation of one or more muscles of the patient.

32. The method of any of claim 17, wherein the selectable set of motor neurons are established based on the first and second sets of positions.

33. The method of any of claim 17, wherein the first frequency is about 20,000 Hz and the frequency difference being in the range of 0.1 to 200 Hz.

34. The method of claim 17, wherein the first set of electrodes are secured subcutaneously proximate the C3 vertebra of the patient and the second set of electrodes are secured subcutaneously proximate the C5 vertebra of the patient.

35. A computer program product, the computer program product comprising at least one non-transitory computer-readable storage medium having computer-executable program code instructions stored therein, the computer-executable program code instructions comprising program code instructions configured to, when executed by a controller:
    cause a first signal generator to generate a first electrical signal; and
    cause a second signal generator to generate a second electrical signal;
    wherein:
        the first electrical signal is configured to be applied to a first set of electrodes, which are configured to be secured to a first set of positions on the patient proximate a C3 vertebra of the patient, the second electrical signal is configured to be applied to a second set of electrodes, which are configured to be secured to a second set of positions on the patient proximate a C5 vertebra of the patient,
        the first electrical signal is a periodic signal of a first frequency, the second electrical signal is a periodic signal of a second frequency, the first frequency and the second frequency differ by a frequency difference that produces a temporal interference pattern between the first frequency and the second frequency, and wherein providing the first signal to the first electrodes and the second signal to the second electrodes excites a selected set of motor neurons of the patient causing excitation of a diaphragm of the patient.

36. The computer program product of claim 35, wherein the first frequency is about 20,000 Hz and the frequency difference being in the range of 0.1 to 200 Hz.

37. The computer program product of claim 35, wherein the first set of electrodes are secured subcutaneously proximate the C3 vertebra of the patient and the second set of electrodes are secured subcutaneously proximate the C5 vertebra of the patient.

* * * * *